(12) United States Patent
Aundal

(10) Patent No.: US 7,416,542 B2
(45) Date of Patent: *Aug. 26, 2008

(54) OPEN CIRCUIT GRAVITY-ASSISTED UROFLOWMETER

(75) Inventor: Knud Torp Aundal, Roskilde (DK)

(73) Assignee: Medtronic, Inc., Minneapolis, MN (US)

( * ) Notice: Subject to any disclaimer, the term of this patent is extended or adjusted under 35 U.S.C. 154(b) by 574 days.

This patent is subject to a terminal disclaimer.

(21) Appl. No.: 10/837,032

(22) Filed: Apr. 30, 2004

(65) Prior Publication Data

US 2005/0256428 A1    Nov. 17, 2005

(51) Int. Cl.
*A61M 1/00* (2006.01)
*A61B 10/00* (2006.01)
*A61B 5/00* (2006.01)
*B65D 81/00* (2006.01)
*G01F 1/58* (2006.01)
*G01F 1/56* (2006.01)

(52) U.S. Cl. .................. 604/317; 604/318; 604/325; 73/861.08; 73/861.12; 73/861.13; 600/419; 600/504; 600/570; 600/573; 600/575; 600/576; 600/580

(58) Field of Classification Search .......... 604/317, 604/318, 325; 600/570–580, 576, 575, 573, 600/504, 419; 73/861.13, 861.12, 861.08
See application file for complete search history.

(56) References Cited

U.S. PATENT DOCUMENTS

| 3,340,733 | A | * | 9/1967 | Lasher | 73/861.74 |
|---|---|---|---|---|---|
| 3,529,591 | A | * | 9/1970 | Schuette | 600/505 |
| 3,734,083 | A | * | 5/1973 | Kolin | 600/505 |
| 4,008,609 | A | | 2/1977 | Lambrecht et al. | |
| 4,051,431 | A | * | 9/1977 | Wurster | 73/861 |
| 4,099,412 | A | | 7/1978 | Nehrbass | |
| 4,118,981 | A | | 10/1978 | Cave | |
| 4,145,924 | A | | 3/1979 | Müller | |
| 4,236,410 | A | * | 12/1980 | Appel et al. | 73/861.12 |
| 4,434,667 | A | | 3/1984 | August et al. | |
| 4,459,858 | A | * | 7/1984 | Marsh | 73/861.12 |
| 4,554,687 | A | * | 11/1985 | Carter et al. | 4/144.2 |
| 4,554,828 | A | * | 11/1985 | Doll | 73/202 |
| 4,683,748 | A | | 8/1987 | Carter | |
| 4,732,160 | A | | 3/1988 | Ask et al. | |
| 4,881,413 | A | | 11/1989 | Georgi et al. | |
| 4,891,993 | A | * | 1/1990 | Barker | 73/863.52 |
| 4,899,592 | A | | 2/1990 | Behrens | |
| 5,046,510 | A | * | 9/1991 | Arns et al. | 600/584 |
| 5,062,304 | A | * | 11/1991 | Van Buskirk et al. | 73/861 |

(Continued)

OTHER PUBLICATIONS

Danfoss Industriel Instrumentering, Simply More, Product Brochure, 5 pages, Denmark.

(Continued)

*Primary Examiner*—T. Zalukaeva
*Assistant Examiner*—Ginger T Chapman
(74) *Attorney, Agent, or Firm*—Mary P. Bauman

(57) ABSTRACT

An open circuit gravity-assisted uroflowmeter has a urine collector having a generally open inlet in fluid communication with a sensing passage located at a lower elevation than the inlet, the sensing passage intersecting a magnetic field and having electrodes for detecting a flow-dependent voltage induced by the passage of urine through the magnetic field. Preferred embodiments of the uroflowmeter may have low pressure drop, rapid response and simple construction.

22 Claims, 6 Drawing Sheets

U.S. PATENT DOCUMENTS

| | | | |
|---|---|---|---|
| 5,078,012 A * | 1/1992 | Ding et al. | 73/861.74 |
| 5,176,148 A | 1/1993 | Wiest et al. | |
| 5,207,105 A | 5/1993 | Fukunaga et al. | |
| 5,325,728 A | 7/1994 | Zimmerman et al. | |
| 5,327,787 A | 7/1994 | Kiene et al. | |
| 5,495,854 A | 3/1996 | Currie | |
| 5,708,212 A | 1/1998 | Batey | |
| 6,237,424 B1 | 5/2001 | Salmasi et al. | |
| 6,463,807 B1 | 10/2002 | Feller | |
| 6,507,598 B2 | 1/2003 | Tsuda et al. | |
| 6,507,599 B2 | 1/2003 | Tsuda et al. | |
| 6,599,277 B2 * | 7/2003 | Neubert | 604/317 |
| 6,640,649 B1 * | 11/2003 | Paz et al. | 73/861.41 |
| 6,904,809 B1 * | 6/2005 | Aundal | 73/861.08 |
| 6,931,943 B1 * | 8/2005 | Aundal | 73/861.12 |

OTHER PUBLICATIONS

Bailey, Fischer & Porter, Electromagnetic flowmeter, made of stainless steel with pulsed DC technology and integrally mounted converter (compact), Product Descriptions, pp. 1-7.

Medtronic, Inc., Duet© Logic G/2 Product Brochure, 2002.

Beli Technics BV, Beli Technics Brochure, The Netherlands, 6 pages.

Medtronic, Inc., Urodyn© 1000 Accurate Uroflowmetry a Matter of Simple Convenience Product Brochure with Spinning Disk, 4 pages, 2000.

Medtronic, Inc., Urodyn© 1000 Portable Alternative in Uroflow Technology Product Brochure with Weight Cell, 2 pages, 2000.

Endress+Hauser GmbH+Co., Durchflussmesser Flowtec Product Specification, 8 pages.

Endress+Hauser GmbH+Co., Magpac DMI 6230 Product Specification, 6 pages.

Laborie Medical Technologies, Urocap Product Brochure.

Medical Measurement Systems, Uroflowmeter Brochure with Weight Cell, 1 page, Holland.

Andromeda, Ellipse-The modular concept for precise urodynamics, 8 pgs.

* cited by examiner

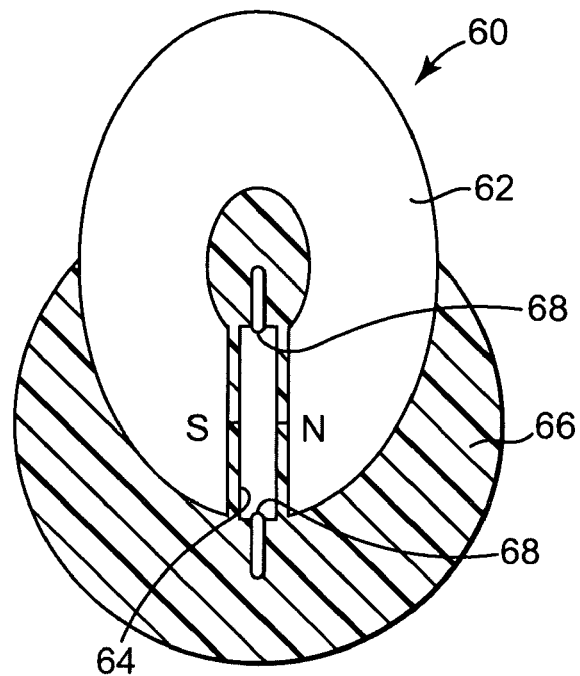
Fig. 6
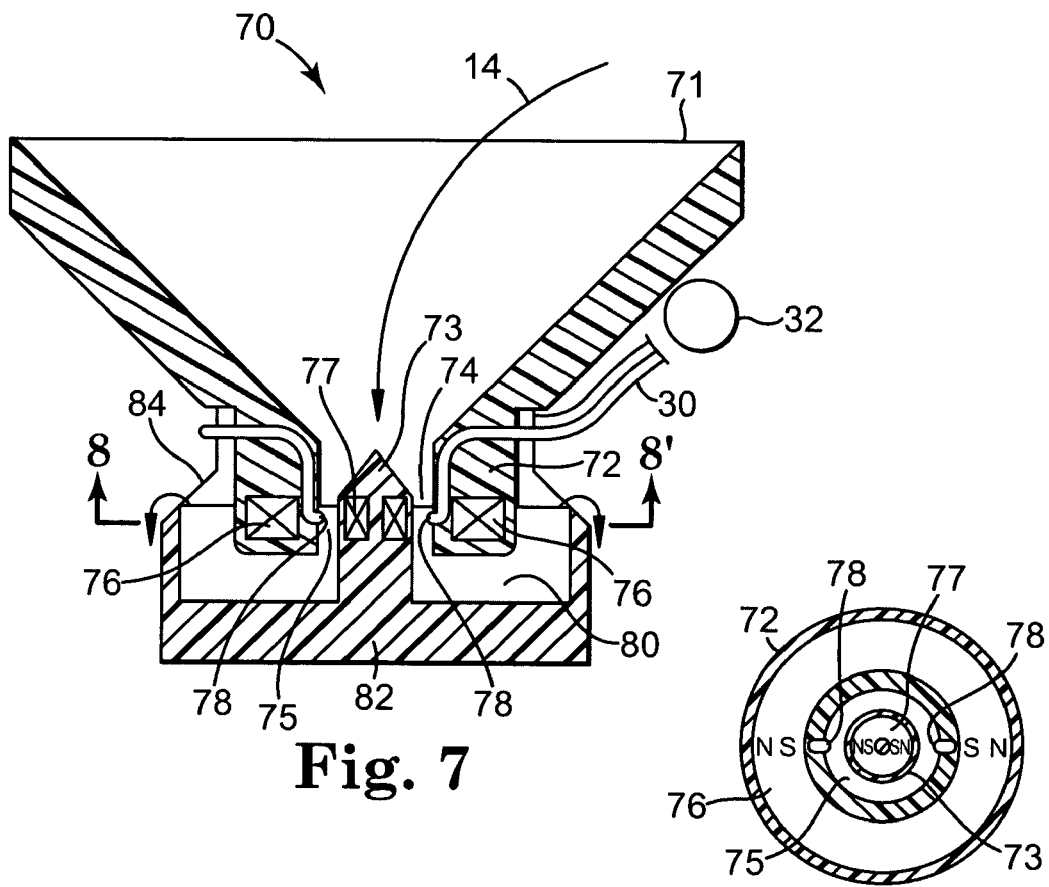
Fig. 7
Fig. 8

OPEN CIRCUIT GRAVITY-ASSISTED UROFLOWMETER

TECHNICAL FIELD

This invention relates to urine discharge measurement.

BACKGROUND

Uroflowmetry devices are used to measure urine discharge flow rates or total discharge volumes for diagnostic or research purposes. A variety of devices have been employed, including weight cells, rotameters, spinning disk or spinning rotor sensors, drop spectrometer sensors, air displacement sensors, capacitive sensors and pressure sensors. References describing such devices include U.S. Pat. Nos. 4,099,412, 4,683,748, 4,732,160, 5,046,510, 5,062,304, 5,078,012, 5,176,148 and 5,495,854.

Other references describing flow measurement devices include U.S. Pat. Nos. 4,008,609, 4,118,981, 4,145,924, 4,434,667, 4,881,413, 4,899,592, 5,207,105, 5,325,728, 5,327,787, 5,708,212, 6,237,424 B1 and 6,463,807 B1.

SUMMARY OF THE INVENTION

Some uroflowmeters are equipped with a receptacle for collecting urine, and require periodic receptacle emptying and replacement or cleaning. Also, some uroflowmeters employ electrically energized or moving parts (e.g., motors) and thus may be prone to failure or wear. Further improvements in one or more factors such as simplicity, compactness, patient isolation, speed of response or accuracy would be desirable in uroflowmeter devices.

The invention provides, in one aspect, an open circuit gravity-assisted uroflowmeter comprising a urine collector having a generally open inlet in fluid communication with a sensing passage located at a lower elevation than the inlet, the sensing passage intersecting a magnetic field and having electrodes for detecting a flow-dependent voltage induced by the passage of urine through the magnetic field.

The invention provides, in another aspect, a method for measuring urine flow comprising (a) passing a stream of urine through an open circuit gravity-assisted uroflowmeter comprising a urine collector having a generally open inlet and in fluid communication with a sensing passage located at a lower elevation than the inlet and intersecting a magnetic field, and (b) monitoring a flow-dependent voltage induced by the passage of urine through the magnetic field.

These and other aspects of the invention will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWING

FIG. 6 is a sectional plan view of a disclosed device employing a horseshoe magnet.

FIG. 7 is a sectional side view of a disclosed device employing ring magnets.

FIG. 8 is a sectional plan view of the FIG. 7 device, taken along the line 8-8'.

DETAILED DESCRIPTION

Figure 1:
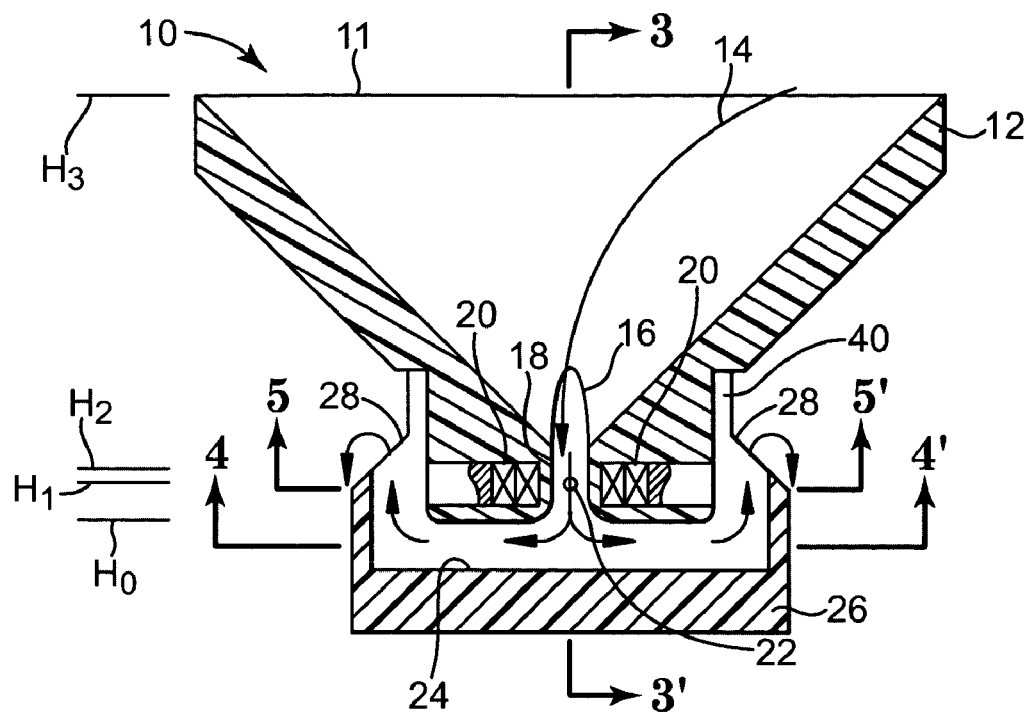
FIG. 1 is a sectional side view of a disclosed uroflowmeter device.

When used to describe the elevation, location, orientation or motion of elements or liquids in the disclosed devices, words such as "upward", "downward", "higher", "lower", "above", "below" and the like refer to the relative position of an element or liquid portion with respect to another element or liquid portion when the disclosed device is being used in its normal orientation for measurement of liquid flow, and are not intended to require that the disclosed devices should have any particular orientation in space during manufacture or storage.

When used with respect to a liquid flow measurement device, the phrase "gravity-assisted" refers a generally downward liquid flow path from an initial higher elevation upon entry into the device to an eventual lower elevation upon exit from (or settling within) the device.

The phrase "in fluid communication" refers to an available liquid flow path from a first region or location in a device to a second region or location in the device.

The phrase "in enclosed fluid communication" refers to an available enclosed liquid flow path from a first region or location in a device to a second region or location in the device.

When used with respect to a liquid flow measurement device, the phrase "open circuit" refers to a device having an open inlet collector (e.g., a funnel) into which a liquid to be measured is directed.

When used with respect to a liquid flow measurement device, the phrase "closed circuit" refers to a device that is in enclosed fluid communication with a source of liquid to be measured.

The phrase "sensing passage" refers to a conduit or other liquid passageway in which a liquid flow rate is to be determined.

When used with respect to a sensing passage, the phrase "intersecting a magnetic field" refers to an orientation of the sensing passage and a nearby magnetic field such that a voltage will be induced in a conductive liquid as the liquid passes through the sensing passage.

When used with respect to a sensing passage that intersects a magnetic field, the phrase "sensing passage volume" refers to the region between opposing magnet poles that generate the magnetic field.

When used with respect to a sensing passage in a liquid flow measurement device, the phrase "integral trap" refers to a device that as supplied to the user (and without the installation of a wet leg plumbing run or other external trap) has a liquid flow path whose outlet elevation is such that the sensing passage will normally remain filled with liquid after a first use or first rinsing, and will normally only require top-up or replacement of such liquid to accommodate evaporation or cleaning.

When used with respect to a liquid flow measurement device, the word "passive" refers to a device that does not require an external or onboard power supply to measure liquid flow rates. By way of example, liquid flow measurement devices having spinning disks, spinning rotor sensors, or electromagnets but no permanent magnets would not ordinarily be regarded as passive devices. By way of further example, liquid flow measurement devices having electrodes supplied with a biasing voltage and not requiring other external or onboard power may ordinarily be regarded as passive devices.

Referring to FIG. 1, a preferred embodiment of the disclosed uroflowmeter is shown in sectional plan view. Uroflowmeter 10 has an upward-facing generally open inlet 11 having elevation $H_3$. Generally funnel-shaped urine collector 12 collects a stream of urine 14 and directs it into opening 16. The collected urine falls through sensing passage 18 past generally opposed permanent bar magnets 20 and generally opposed electrodes 22 (one of which is shown in FIG. 1). The electrodes 22 are at elevation $H_1$. Elevation $H_1$ may be lower than elevation $H_3$, a factor that assists in providing rapid gravity-assisted transport of the collected urine stream past the magnets 20 and electrodes 22. The collected urine next travels through generally horizontal passageway 24 in base 26, and exits uroflowmeter 10 through outlet openings 28.

The urine can be collected in a suitable receptacle or discarded. In a preferred embodiment uroflowmeter 10 is mounted or suspended over or in a toilet bowl (not shown in FIG. 1) so that the urine falls from the uroflowmeter into the toilet bowl during use. Passageway 24 and the openings 28 may for example be sufficiently large to minimize back pressure and to avoid delayed removal of the falling urine stream from sensing passage 18, but sufficiently small to provide rapid uroflowmeter response. The lowermost edges of openings 28 are at elevation $H_2$ and the top of passageway 24 is at elevation $H_0$. Elevation $H_2$ may be lower than elevation $H_3$ and higher than elevations $H_1$ and $H_0$, factors that help permit passageway 24 to function as part of a generally annular integral trap with (in this embodiment) multiple outlets. Passageway 24 directs the flow of liquid outwardly with respect to sensing passage 18 and maintains standing liquid (e.g., urine, water or other liquid that may have been used to rinse uroflowmeter 10) in sensing passage 18 at a height sufficient to keep electrodes 22 wet. Maintaining electrodes 22 in a wet state helps to speed the uroflowmeter's response and provide more accurate readings, particularly during the early stages of urine discharge. Outlet elevation $H_2$ may be sufficiently higher than elevation $H_1$ so that all of sensing passage 18 normally remains filled with liquid. This may provide yet faster response or better accuracy. Preferably however outlet elevation $H_2$ is not so high as to cause excessive back pressure downstream from sensing passage 18.

Elevation $H_2$ may instead be the same as or less than elevation $H_1$. For example, the electrodes 22 may have a sufficiently higher elevation $H_1$ than the elevation $H_2$ of openings 28 so that the electrodes 22 may dry out between uses. Also, the electrodes 22 may have the same or only a slightly higher elevation $H_1$ than the elevation $H_2$ of openings 28, and may be maintained in a wet state between uses by capillary forces, sensing passage surface treatments near the electrodes 22 or other suitable measures that enable liquid in sensing passage 18 to reach the electrodes 22.

Figure 2:
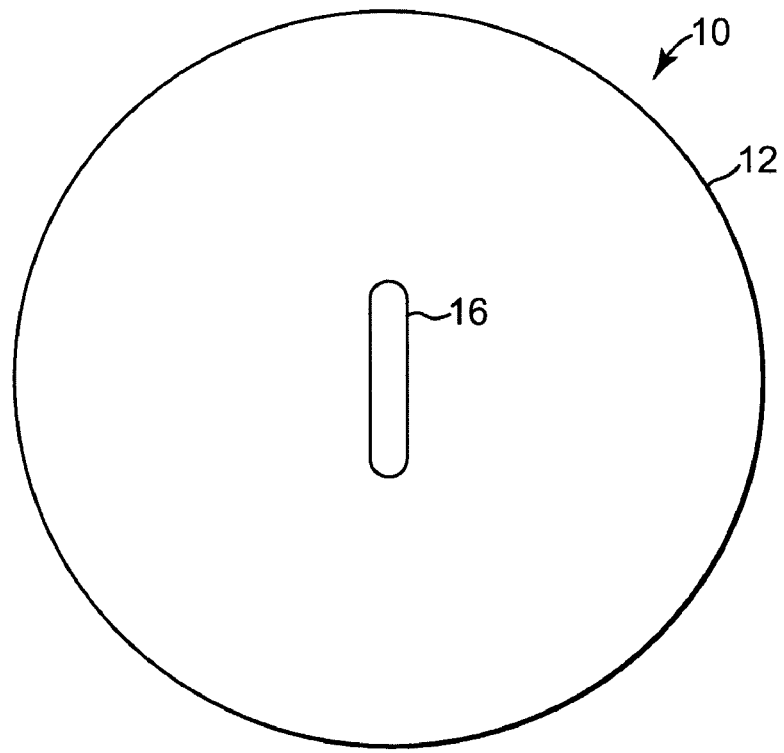
FIG. 2 is a plan view of the FIG. 1 device.

FIG. 2 shows a plan view of collector 12. Opening 16 is generally elongated and may be made sufficiently large to minimize back pressure and liquid buildup in collector 12 and delayed delivery of the falling urine stream to sensing passage 18.

Figure 3:
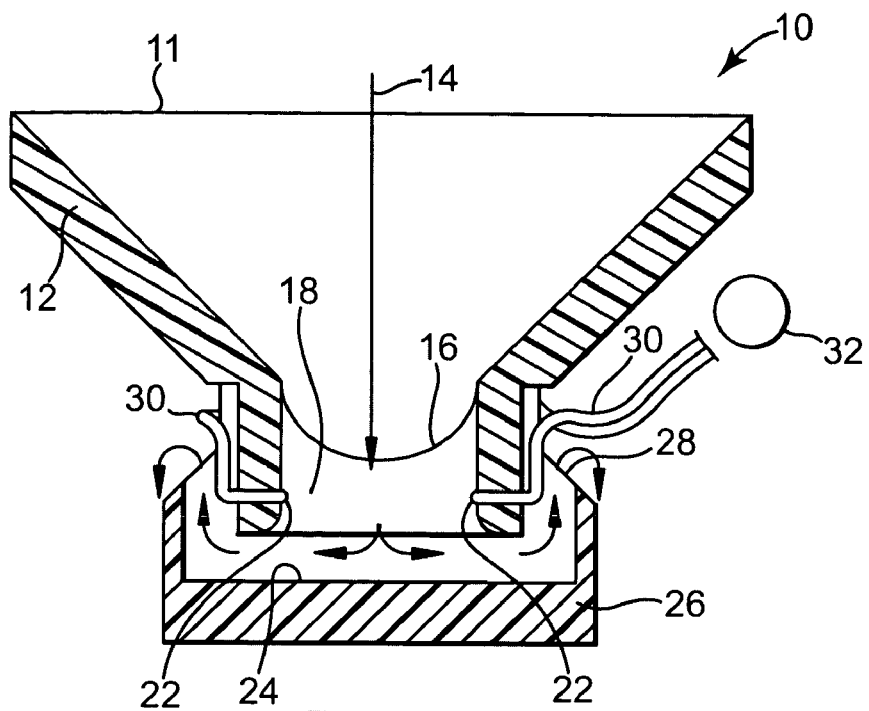
FIG. 3 is a sectional side view of the FIG. 1 device, taken along the line 3-3'.

FIG. 3 is a sectional side view of uroflowmeter 10 taken through line 3-3' in FIG. 1. The generally opposed relationship of electrodes 22 may more readily be seen in FIG. 3 than in FIG. 1. Leads 30 permit voltage readings from electrodes 22 to be connected to a voltmeter or other suitable electronic circuit 32. The design and construction of such a circuit will be familiar to those skilled in the art.

When urine passes through the magnetic field between magnets 20, a flow-dependent voltage is induced between electrodes 22. The urine flow rate may be calculated based on Faraday's law of magnetic induction (which states that the voltage induced across a conductor as it moves at right angles through a magnetic field is proportional to the conductor's velocity), using the equation:

$$V = B \times D \times c$$

where
V is the detected voltage (Volts)
B is the magnetic flux density (Tesla)
D is the distance between the electrodes (mm) and
c is the mean flow velocity (mm/sec).

Figure 4:
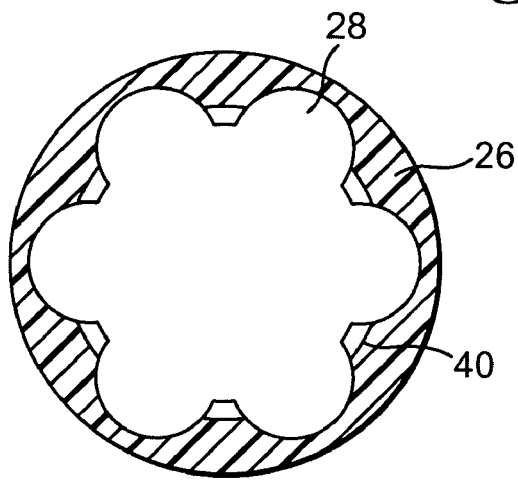
FIG. 4 is a sectional plan view of the FIG. 1 device, taken along the line 4-4'.

FIG. 4 is a sectional plan view taken along line 4-4' in FIG. 1. Openings 28 are arranged around base 26 and between projections 40. Projections 40 grip collector 12 (e.g., using a friction fit) and may permit disassembly of collector 12 and base 26 if desired (e.g., for cleaning or maintenance).

Figure 5:
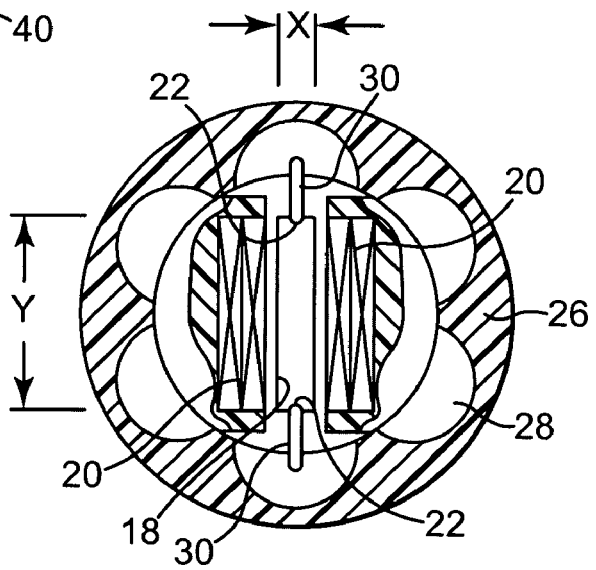
FIG. 5 is a sectional plan view of the FIG. 1 device, taken along the line 5-5'.

FIG. 5 is a sectional plan view taken along line 5-5' in FIG. 1. Sensing passage 18 has a minor axis X and major axis Y. Minor axis X is generally aligned with the permanent magnetic field between magnets 20, and for a given cross-sectional area in sensing passage 18 will provide a stronger magnetic field through sensing passage 18 than would be the case if sensing passage 18 had a circular cross-section. Major axis Y is generally aligned with electrodes 22, and for a given cross-sectional area in sensing passage 18 will provide a longer signal path than would be the case if sensing passage 18 had a circular cross-section. Both the short X axis and the long Y axis may contribute to improved flowmeter sensitivity or accuracy.

FIG. 6 shows a sectional plan view taken through the magnet portion of another disclosed uroflowmeter 60. Horseshoe magnets 62 may provide a stronger magnetic field through sensing passage 64 then might normally be achieved using bar magnets such as magnets 22. A stronger magnetic field may permit more latitude in the design of electrodes 68 or in the associated electronic circuitry. Suitable cutouts or other reliefs may be formed in base 66 to accommodate magnet 62.

FIG. 7 shows a sectional side view of another disclosed uroflowmeter 70, and FIG. 8 shows a sectional plan view taken along line 8-8' in FIG. 7. Uroflowmeter 70 has an upward-facing generally open inlet 71. Generally funnel-shaped urine collector 72 collects a stream of falling urine 14 and directs it past central post 73 into opening 74. The collected urine falls through sensing passage 75 past permanent ring magnet 76 (mounted in collector 72), permanent ring magnet 77 (mounted in post 73) and generally opposed electrodes 78. The collected urine next travels through generally horizontal passageway 80 in base 82, and exits uroflowmeter 70 through openings 84. Magnets 76 and 77 may be disposed in an annular arrangement that may provide a compact sensing passage that intersects a high strength permanent magnetic field.

Figure 9:
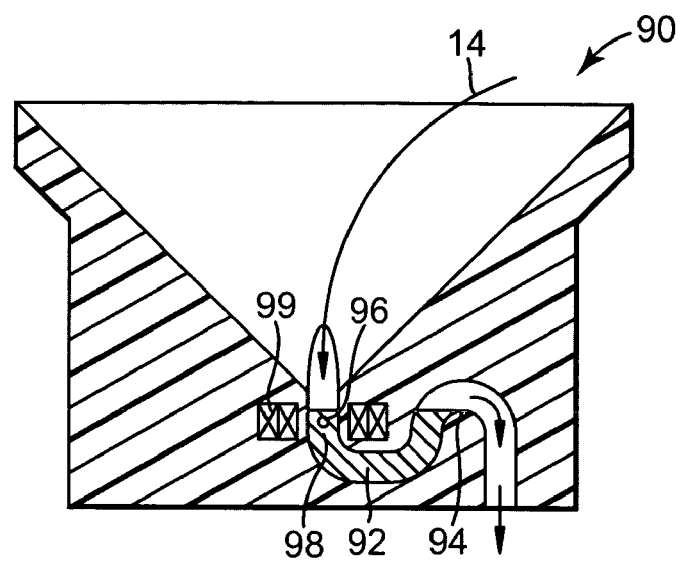
FIG. 9 is a sectional side view of a disclosed uroflowmeter device employing an integral trap.

FIG. 9 shows a sectional side view of another disclosed uroflowmeter 90. Uroflowmeter 90 includes an integral, generally planar trap section 92 whose outlet 94 has an elevation sufficient to maintain electrodes 96 in sensing passage 98 in a wet condition. As illustrated, outlet 94 has an elevation sufficient to maintain the liquid level in sensing passage 98 approximately as high as that of permanent bar magnets 99. This may further contribute to improved uroflowmeter accuracy or faster response.

Figure 10:
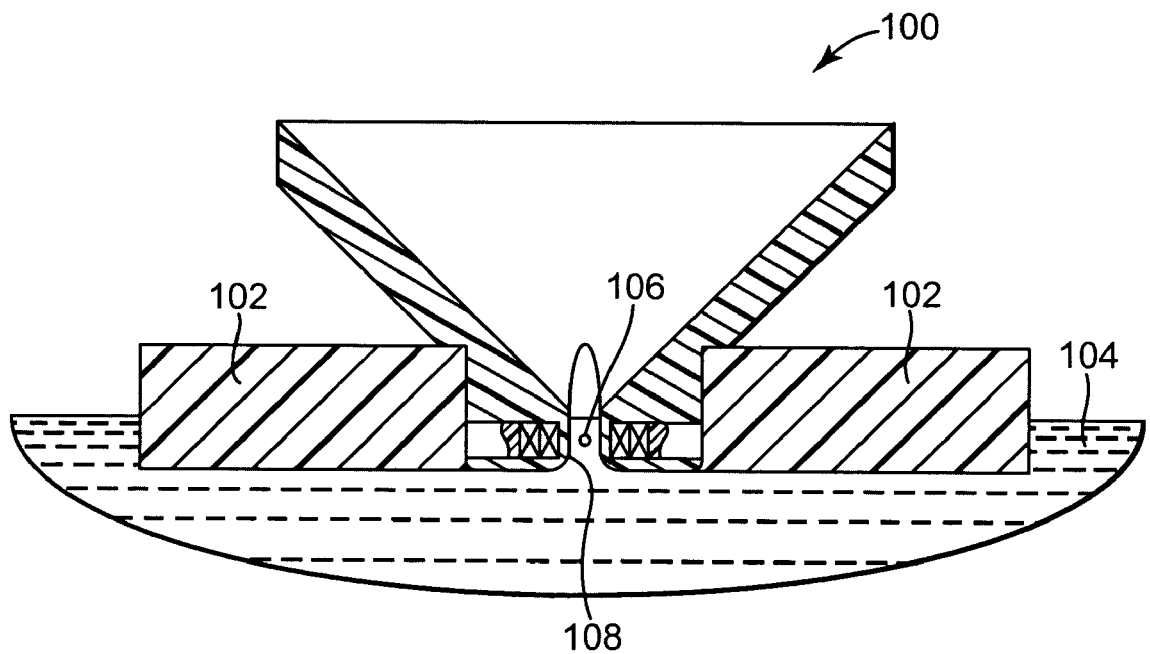
FIG. 10 is a sectional side view of a disclosed floating uroflowmeter device having a submerged sensing passage.

FIG. 10 shows a sectional side view of another disclosed uroflowmeter 100. Uroflowmeter 100 has floats 102 that permit uroflowmeter 100 to rest upon the surface of water 104 (e.g., in a toilet bowl, not shown in FIG. 10) while maintaining electrodes 106 in sensing passage 108 in a wet condition.

Figure 11:
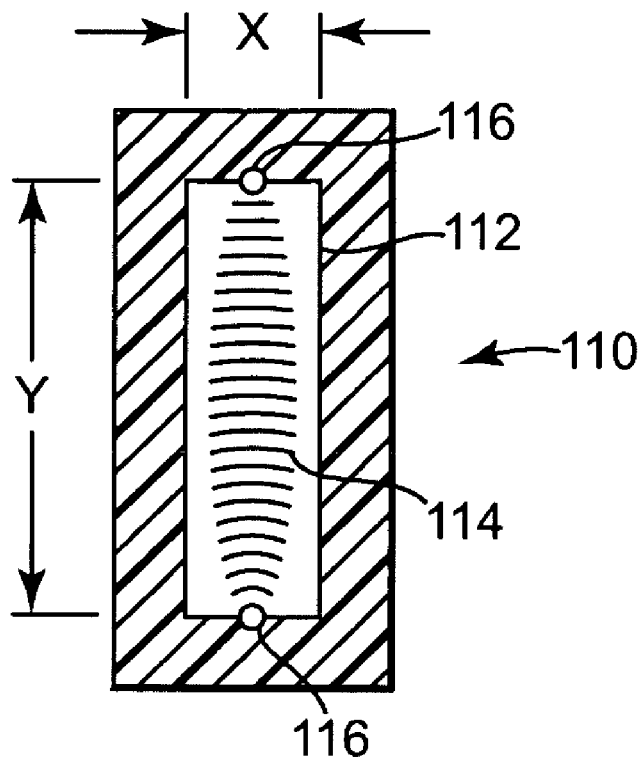
FIG. 11 is a cross-sectional view of a rectangular sensing passage.
Figure 12:
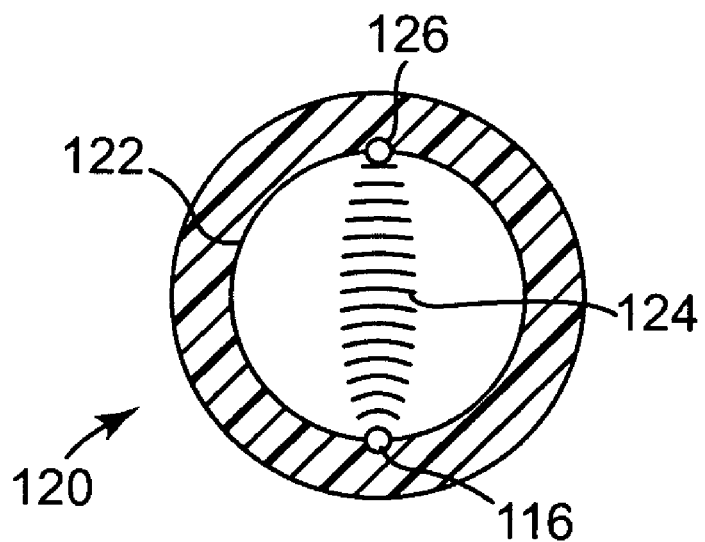
FIG. 12 is a cross-sectional view of a circular sensing passage.

The sensing passage can have a variety of shapes and sizes. For example, FIG. 11 shows a portion of a uroflowmeter 110 whose sensing passage 112 has a rectangular cross-section. Minor axis X is generally aligned with an applied magnetic field 114 (shown schematically in FIG. 11) and major axis Y generally aligned with electrodes 116. As a further example, FIG. 12 shows a portion of a uroflowmeter 120 whose sensing passage 122 has a circular cross-section. Applied magnetic field 124 (shown schematically in FIG. 12) is generally orthogonal to the axis defined by electrodes 126 and the flow of liquid through sensing passage 122. Other sensing passage shapes (e.g., ovals, ellipses or dogbone shapes, or elongated openings with generally straight sides and rounded corners, e.g., as shown in FIG. 5) can readily be envisioned by those skilled in the art.

The disclosed uroflowmeters may be manufactured in a variety of shapes and sizes. For example, the uroflowmeter shown in FIG. 1 may have an inlet diameter of about 10 to about 40 cm (e.g., about 30 cm), and a base diameter (viz., the diameter of a cross-section taken through the sensing passage midpoint, perpendicular to the liquid flow direction) of about 10 to about 60 mm (e.g., about 40 mm). The sensing passage volume may be relatively small, e.g., less than about 1 cm$^3$. It will be appreciated by those skilled in the art that a conductive liquid may be affected by the magnetic field in a region somewhat larger than the region between the opposing magnet poles. If a noncircular sensing passage is employed, it may have a variety of shapes and may for example be an ellipse or oval having a minor axis X of about 1 to about 5 mm (e.g., about 3 mm), and a major axis Y of about 5 to about 20 mm (e.g., about 13 mm). Additional details regarding passive noncircular sensing passage flowmeters may be found in copending application Serial No. (attorney docket number 151-P-11766.00US) filed even date herewith, the disclosure of which is incorporated herein by reference. If an integral trap is employed, it may have a variety of shapes and may for example have a volume of about 1 to about 5 cm$^3$ (e.g., about 2 cm$^3$), with the integral trap volume being defined as the downstream region from the sensing passage volume to the device outlet. Additional details regarding integral trap flowmeters may be found in copending application Serial No. (attorney docket number 151-P-11767.00US) filed even date herewith, the disclosure of which is incorporated herein by reference. The disclosed uroflowmeters may accommodate a variety of flow rates, e.g. from about 0.5 ml/sec to about 50 ml/sec.

The uroflowmeter body may be manufactured from a variety of transparent or opaque materials. Suitable materials include plastics (e.g., polyethylene, polypropylene, polyvinyl chloride, polycarbonate or ABS), nonmagnetic metals (e.g., aluminum, brass or nonmagnetic stainless steel), glasses or ceramics (e.g., porcelain).

The magnets may be permanent magnets (made, for example, from NdFeB (neodymium-iron-boron), ferrite, AlNiCo (aluminum-nickel-cobalt) or SmCo (samarium cobalt)). The magnets may also be electromagnets or a combination of both permanent magnets and electromagnets. The permanent magnets may have magnetic strengths ranging for example from about 0.5 Tesla to about 1.5 Tesla (e.g., 1.3 Tesla) as measured at a pole surface. Passive transducers having a sufficiently strong permanent magnetic field to carry out flow rate measurements are especially preferred, as they do not require excitation power and may employ only direct current sensing connections, thus facilitating patient isolation. If equipped with an electromagnet, the disclosed uroflowmeters may employ an internal or external power source.

Figure 13:
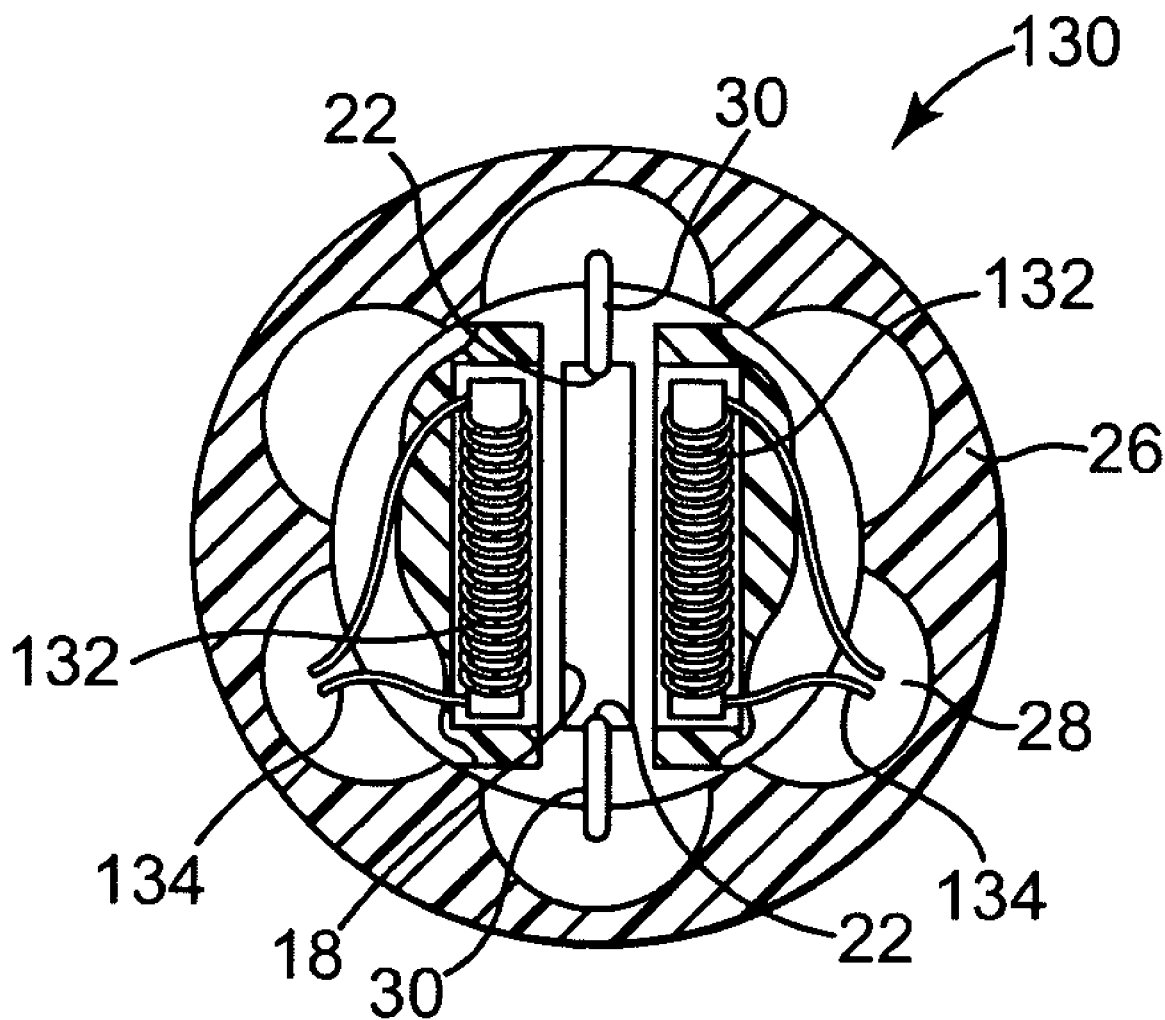
FIG. 13 is a sectional plan view of a disclosed device employing electromagnets.

FIG. 13 is a sectional plan view of a disclosed uroflowmeter 130 employing components like those shown in the uroflowmeter of FIG. 5 but using electromagnets 132 in place of permanent magnets 20. Electromagnets 132 may be energized via leads 134.

The electrodes may be made from a variety of materials. Suitable materials include corrosion-resistant materials such as gold or silver; gold- or silver-plated metals (e.g., silver-plated brass or copper, with the silver plating preferably being oxidized); or less corrosion-resistant (but also less expensive) materials such as copper or brass.

The disclosed uroflowmeters may be disposable or reusable. Owing to the simplicity of the design and the relatively compact dimensions that may be employed, the disclosed uroflowmeters are particularly well-suited for disposable use. The disclosed uroflowmeters may include a separate or detachable (and optionally disposable) inlet funnel. The disclosed uroflowmeters may also include a receptacle or other large reservoir to collect all of the discharged urine. Preferably the disclosed uroflowmeters do not include such a reservoir and do not require emptying or other maintenance beyond a simple rinsing step. Preferably the disclosed uroflowmeters do not have moving parts or resilient seals. The disclosed uroflowmeters may however include fixing devices, stands or other components that facilitate the uroflowmeter's mounting or use, e.g., by mounting or supporting the uroflowmeter on, in or over a toilet. The uroflowmeter may be mounted or supported in such a way that it automatically will be rinsed when the toilet is flushed.

Various modifications and alterations of this invention will be apparent to those skilled in the art without departing from the scope and spirit of this invention. It should be understood that this invention is not limited to the illustrative embodiments set forth above.

I claim:

1. An open circuit gravity-assisted uroflowmeter comprising a urine collector having a generally open inlet in fluid communication with a sensing passage located at a lower elevation than the inlet, the sensing passage intersecting a magnetic field and having electrodes for detecting a flow-dependent voltage induced by the passage of urine through the magnetic field.

2. A uroflowmeter according to claim 1 having a body comprising plastic.

3. A uroflowmeter according to claim 1 wherein the magnetic field is provided by one or more permanent magnets.

4. A uroflowmeter according to claim 1 wherein the magnetic field is provided by bar magnets.

5. A uroflowmeter according to claim 1 wherein the magnetic field is provided by a horseshoe magnet.

6. A uroflowmeter according to claim 1 wherein the magnetic field is provided by annularly disposed ring magnets.

7. A uroflowmeter according to claim 1 wherein the magnetic field is provided by one or more electromagnets.

8. A uroflowmeter according to claim 1 wherein the sensing passage has a volume less than about 1 cm$^3$.

9. A uroflowmeter according to claim 1 wherein the inlet has a diameter of about 10 to about 40 cm.

10. A uroflowmeter according to claim 1 that does not include a reservoir to collect all of the urine.

11. A uroflowmeter according to claim 1 further comprising a fixing device, stand or other component that mounts or supports the uroflowmeter on, in or over a toilet.

12. A uroflowmeter according to claim 11 wherein the uroflowmeter is rinsed when the toilet is flushed.

13. A uroflowmeter according to claim 1 having no moving parts or resilient seals.

14. A method for measuring urine flow comprising (a) passing a stream of urine through an open circuit gravity-assisted uroflowmeter comprising a urine collector having a generally open inlet and in fluid communication with a sensing passage located at a lower elevation than the inlet and intersecting a magnetic field, and (b) monitoring a flow-dependent voltage induced by the passage of urine through the magnetic field.

15. A method according to claim 14 wherein the uroflowmeter has a body comprising plastic.

16. A method according to claim 14 wherein the magnetic field is provided by one or more permanent magnets.

17. A method according to claim 14 wherein the magnetic field is provided by one or more electromagnets.

18. A method according to claim 14 wherein the sensing passage has a volume less than about 1 cm$^3$.

19. A method according to claim 14 wherein the inlet has a diameter of about 10 to about 40 cm.

20. A method according to claim 14 further comprising mounting or supporting the uroflowmeter on, in or over a toilet so that the urine falls from the uroflowmeter into the toilet bowl.

21. A method according to claim 20 further comprising flushing the toilet to rinse the uroflowmeter.

22. A method according to claim 20 wherein the uroflowmeter has no moving parts or resilient seals.

* * * * *